United States Patent [19]

Weitz et al.

[11] 4,049,742

[45] Sept. 20, 1977

[54] RECOVERY OF 1,3-BUTADIENE FROM A C₄-HYDROCARBON MIXTURE

[75] Inventors: Hans-Martin Weitz, Bad Duerkheim; Ulrich Wagner, Limburgerhof; Klaus Volkamer, Frankenthal; Eckart Schubert, Ludwigshafen; Friedhelm Bandermann, Hern, all of Germany

[73] Assignee: BASF Aktiengesellschaft, Ludwigshafen, Germany

[21] Appl. No.: 669,710

[22] Filed: Mar. 23, 1976

[30] Foreign Application Priority Data

Apr. 15, 1975 Germany .............................. 2516362

[51] Int. Cl.² ................................................ C07C 7/08
[52] U.S. Cl. ............................ 260/681.5 R; 260/680 R
[58] Field of Search ............................... 260/681.5, 680

[56] References Cited

U.S. PATENT DOCUMENTS

| | | | |
|---|---|---|---|
| 3,705,204 | 12/1972 | Horie et al. | 260/681.5 R |
| 3,803,258 | 4/1974 | Weitz et al. | 260/681.5 R |

FOREIGN PATENT DOCUMENTS 1,808,259  8/1969  Germany ...................... 260/681.5 R

*Primary Examiner*—Veronica O'Keefe
*Attorney, Agent, or Firm*—Keil, Thompson & Shurtleff

[57] ABSTRACT

1,3-Butadiene is recovered with the aid of a selective solvent from a C₄-hydocarbon mixture containing 1,3-butadiene, hydrocarbons which are more soluble in said selective solvent than 1,3-butadiene, including acetylenes and possibly 1,2-butadiene and C₅-hydrocarbons, and hydrocarbons which are less soluble in said selective solvent than 1,3-butadiene. The C₄-hydrocarbon mixture is separated by the use of one or more extractive distilling zones into a distillate containing the less soluble hydrocarbons, a stream consisting of 1,3-butadiene and a stream containing the more soluble hydrocarbons including the higher acetylenes and 1,3-butadiene, the latter stream being subjected to catalytic hydrogenation.

9 Claims, 1 Drawing Figure

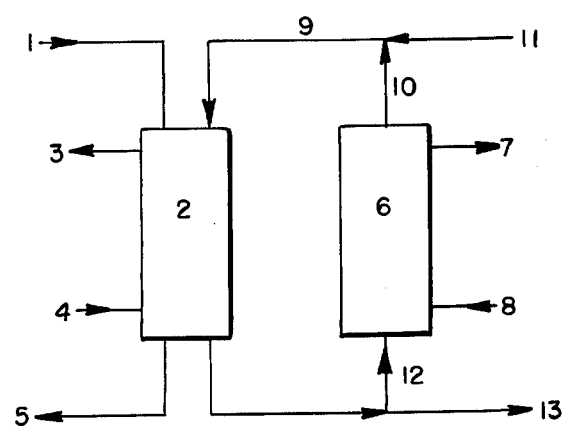

RECOVERY OF 1,3-BUTADIENE FROM A C₄-HYDROCARBON MIXTURE

It is known, for example from German Pat. No. 1,184,334 or German Published Applications Nos. 1,568,876 and 1,568,902, to use a selective solvent to separate a C$_4$-hydrocarbon mixture containing 1,3-butadiene, hydrocarbons which are more soluble in said selective solvent than 1,3-butadiene including higher acetylenes, and hydrocarbons which are less soluble in said selective solvent and 1,3-butadiene, e.g. butanes or butenes, in a cascade of two extractive distilling zones such that a distillate containing the less soluble hydrocarbons such as butanes and butenes and an extract are obtained in the first extractive distilling zone, from which extract there is obtained, after removal of the selective solvent therefrom, a mixture of 1,3-butadiene and the more soluble hydrocarbons including the higher acetylenes. This mixture of 1,3-butadiene and the more soluble hydrocarbons including higher acetylenes gives, after passing through a second extractive distilling zone, a stream of 1,3-butadiene and, after removal of the selective solvent from the extract, a hydrocarbon stream containing the more soluble hydrocarbons including the higher acetylenes. In the prior art process, the explosive nature of the higher acetylenes and their tendency to form and deposit polymers calls for special precautions when handling the hydrocarbon stream containing said higher acetylenes. For example, the stream containing higher acetylenes is diluted with inert gases, for example inert hydrocarbons, to such an extent that it can then be handled without risk of explosion. Such dilution is generally carried out with butadiene itself by effecting only incomplete separation of the 1,3-butadiene and the higher acetylenes in the final extractive distilling zone. The diluted hydrocarbon stream containing higher acetylenes is usually burnt. However, this process is unsatisfactory, since burning of the said stream causes a loss of the chemical raw materials comprising the hydrocarbons contained in said hydrocarbon stream containing the higher acetylenes and, in addition, the yield of 1,3-butadiene is reduced on account of dilution being effected with 1,3-butadiene. Moreover, the tendency of the hydrocarbon stream containing higher acetylenes to deposit polymers remains even after dilution with an inert hydrocarbon.

It is an object of the present invention to provide a process for the recovery of 1,3-butadiene using a selective solvent from a C$_4$-hydrocarbon mixture, wherein a higher yield of 1,3-butadiene is obtained and by means of which it is possible to utilize the components contained in the C$_4$-hydrocarbon mixture as chemical raw materials. It is another object of the invention to provide a process in which the tendency to deposit polymers in the hydrocarbon stream containing higher acetylenes and obtained after recovery of the 1,3-butadiene is obviated.

In accordance with the present invention, these and other objects and advantages are achieved in a process for the recovery of 1,3-butadiene, using a selective solvent, from a C$_4$-hydrocarbon mixture containing 1,3-butadiene, hydrocarbons which are more soluble in said selective solvent than 1,3-butadiene, including higher acetylenes and possibly 1,2-butadiene and C$_5$-hydrocarbons, and hydrocarbons which are less soluble in said selective solvent than 1,3-butadiene, wherein the C$_4$-hydrocarbon mixture is separated, using one or more extractive distilling zones, into a distillate containing the less soluble hydrocarbons, a stream consisting of 1,3-butadiene and a stream containing the more soluble hydrocarbons including the higher acetylenes and 1,3-butadiene, which stream containing the more soluble hydrocarbons including higher acetylenes and 1,3-butadiene is subjected to catalytic hydrogenation.

According to our novel process, the stream containing the higher acetylenes gives a hydrocarbon stream which may be handled without danger and produces no polymer deposits. In a particularly advantageous embodiment, the process is carried out such that the stream containing the more soluble hydrocarbons including higher acetylenes and 1,3-butadiene is subjected to selective catalytic hydrogenation, the hydrocarbon stream obtained after said hydrogenation being recycled to the starting C$_4$-hydrocarbon mixture. The selective catalytic hydrogenation is advantageously carried out under such conditions that the carbon-carbon triple bonds in the higher acetylenes are hydrogenated to carbon-carbon double bonds. In this way, for example, vinylacetylene is converted to 1,3-butadiene. This method gives a distinctly higher yield of 1,3-butadiene over the prior art process for the recovery of 1,3-butadiene from C$_4$-hydrocarbon mixtures.

The C$_4$-hydrocarbon mixtures to be used in the present invention for the recovery of 1,3-butadiene are for example hydrocarbon fractions obtained in the manufacture of ethylene and/or propylene by thermal cracking of a petroleum fraction such as liquefied petroleum gas, naphtha and gas oil. Such C$_4$-fractions are also obtained in the catalytic dehydrogenation of n-butane and/or n-butene. The C$_4$-hydrocarbon mixture usually contains butanes, n-butene, isobutene, 1,3-butadiene, vinylacetylene, ethylacetylene, 1,2-butadiene and possibly small amounts of C$_5$-hydrocarbons.

Suitable selective solvents are carboxamides such as dimethylformamide, diethylformamide, dimethylacetamide, formylmorpholine, acetonitrile, furfural, N-methylpyrrolidone, butyrolactone, acetone and mixtures thereof with water. It is particularly advantageous to use N-methylpyrrolidone as selective solvent.

The hydrocarbons which are more soluble in the selective solvent than 1,3-butadiene are for example vinylacetylene, ethylacetylene and 1,2-butadiene. Examples of hydrocarbons which are less soluble in the selective solvent than 1,3-butadiene are the butanes, the n-butenes and isobutene. The process may be carried out using only one extractive distilling zone. It is particularly advantageous, however, to carry out the process for the recovery of 1,3-butadiene using a cascade of two extractive distilling zones, using the same selective solvent in each case. In this case, for example, a distillate containing the less soluble hydrocarbons is obtained in the first stage of extractive distillation, the extract consisting of 1,3-butadiene, the more soluble hydrocarbons and the selective solvent. The selective solvent is removed from this extract to give a mixture of 1,3-butadiene and the more soluble hydrocarbons. This mixture is passed through a second extractive distilling zone to undergo further extractive distillation with the selective solvent, giving 1,3-butadiene as distillate and an extract containing the more soluble hydrocarbons including the higher acetylenes and a residue of 1,3-butadiene and the selective solvent. The selective solvent is removed from said extract giving a hydrocarbon stream containing the more soluble hydrocarbons including the higher acetylenes and 1,3-butadiene.

The said stream containing the more soluble hydrocarbons including higher acetylenes and 1,3-butadiene, which is to undergo catalytic hydrogenation according to the present invention, generally has a content of acetylenes of from 1.5 to 70% and preferably from 5 to 70% and more preferably from 10 to 60%, by weight. Hydrogenation is generally carried out using hydrogen conventionally employed for hydrogenation reactions, for example commercially pure hydrogen. The hydrogen may be used undiluted or diluted with an inert gas such as nitrogen. It is preferred to use the hydrogen without the addition of inert gas. However, if the hydrogen used for hydrogenation is diluted with an inert gas, the ratio, by volume, of inert gas to hydrogen is generally from 1:10,000 to 4:1 and preferably from 1:1,000 to 2.5:1.

Hydrogenation may be carried out in the gas phase or in the liquid phase. We prefer to carry out hydrogenation in the liquid phase. The stream to be hydrogenated and containing the more soluble hydrocarbons including the higher acetylenes and 1,3-butadiene may be subjected to hydrogenation as such. Preferably, however, this stream is diluted with an inert solvent. Suitable inert solvents are for example esters such as ethyl acetate, alcohols such as ethanol, propanol and butanol, and ethers. It is particularly advantageous to use the selective solvent employed in the extractive distillation and/or a mixture of saturated and/or monoolefinically unsaturated hydrocarbons as inert solvent for said hydrogenation. A preferred mixture of saturated and/or monoolefinically unsaturated hydrocarbons is the distillate containing the less soluble hydrocarbons as obtained in the extractive distillation. When diluting with an inert solvent, the inert solvent is generally used in amounts of from 0.5 to 50% and preferably from 1 to 30% and more preferably from 1 to 20%, by weight of the hydrocarbon stream to be hydrogenated.

Hydrogenation may be carried out adiabatically or isothermally, but the reaction is preferably carried out isothermally. The reaction is advantageously carried out at temperatures of from 5° to 60° C and preferably from 10° to 45° C. Pressures of from 2.5 to 10 and preferably from 3 to 5 atmospheres are generally used. The hydrocarbon stream to be hydrogenated and the hydrogenating hydrogen may be used cocurrently or countercurrently.

The $C_4$-hydrocarbon mixtures used as starting material generally contain 1,2-butadiene and small amounts of $C_5$-hydrocarbons, some or all of which pass, during separation of the $C_4$-hydrocarbons mixture, into the stream containing the more soluble hydrocarbons including the higher acetylenes and 1,3-butadiene and destined to undergo catalytic hydrogenation according to the present invention. Since the hydrocarbons stream obtained after hydrogenation is recycled to the starting $C_4$-hydrocarbon mixture, there may be gradual accumulation of 1,2-butadiene and $C_5$-hydrocarbons. In order to avoid such accumulation, it may be necessary to remove the 1,2-butadiene and $C_5$-hydrocarbons from the hydrocarbon stream obtained after hydrogenation, by distillation.

A preferred embodiment of the present invention consists in cooling the bleed stream of the hydrogenated hydrocarbon stream and recycling said bleed stream to the inlet of the hydrogenation zone, where it is mixed with the unhydrogenated hydrocarbon mixture which may or may not be diluted with the mixture of saturated and/or monoolefinically unsaturated hydrocarbons. Cooling of said hydrogenated hydrocarbon stream is advantageously carried out in a heat exchanger.

In another embodiment of the process, the hydrocarbon stream to be hydrogenated still contains selective solvent. The hydrocarbon stream to be hydrogenated is preferably a stream which has been obtained by the use of a 2-stage extractive distillation technique and is the extract obtained from the second extractive distillation, from which extract none or only a portion of the selective solvent has been removed.

Advantageously, the hydrogenation catalysts used are supported catalysts containing metals in group VIII of the Periodic Table and/or compounds thereof. Suitable metals in group VIII of the Periodic Table are for example cobalt, nickel and, preferably, the noble metals such as palladium and platinum. We particularly prefer to use palladium. Suitable supports are for example activated charcoal, silica gel, alumina, diatomaceous earth, calcium carbonate or mixtures thereof. We prefer to use calcium carbonate and alumina as supporting material. The content of metal in group VIII of the Periodic Table is generally from 0.01 to 5% and preferably from 0.1 to 2%, by weight of the total supported catalyst. The supported catalysts containing a metal in group VIII of the Periodic Table and/or compounds thereof may be used without any further addition. However, we prefer to use supported catalysts which also contain at least one compound of a metal in group II(b) of the Periodic Table. Suitable metals in group II(b) of the Periodic Table are for example zinc and/or cadmium. We prefer to use zinc. The compound of a metal in group II(b) of the Periodic Table is advantageously added in amounts of from 0.05 to 10% and preferably from 0.5 to 4%, by weight of the supported catalyst.

The following Examples serve to illustrate the invention.

EXAMPLE 1

Hydrogenation is carried out using a $C_4$ cut of the following composition (in percentages by volume):

n-butane: 3.35
isobutane: 0.71
isobutene: 18.1
butene: 8.6
cis-butene-2: 6.5
trans-butene-2: 3.85
butadiene-1,2: 3.65
butadiene-1,3: 30.5
vinylacetylene: 21.1
butyne-1: 3.3
remainder ($C_5$-hydrocarbons): 0.34.

The $C_4$ cut to be hydrogenated is that obtained from a two-stage extractive distillation technique using N-methylpyrrolidone as selective solvent, the stream obtained after the second extractive distillation and containing the more soluble hydrocarbon including the higher acetylenes and 1,3-butadiene having been diluted with the distillate from the first extractive distillation. This $C_4$ cut to be hydrogenated is passed through line 11 (see accompanying drawing) and line 9 to the top of the hydrogenation reactor 2 together with the hydrogenating gas (passed through line 1). Unconsumed hydrogenation gas is withdrawn through line 5. A bleed stream of the hydrogenated $C_4$-hydrocarbon mixture is recycled through line 12, heat exchanger 6 and lines 10 and 9. A hydrogenated $C_4$-hydrocarbon mixture is withdrawn through line 13, this having the following composition (in percentages by volume):

n-butane: 3.85
isobutane: 0.65
isobutene: 18.6
butene-1: 15.8
cis-butene-2: 8.7
trans-butene-2: 5.75
butadiene-1,2: 2.8
butadiene-1,3: 39.9
vinylacetylene: 2.4
butyne-1: 1.4
remainder: 0.15.

The hydrogenation reactor 2 is cooled with cooling water passing through lines 3 and 4 and the heat exchanger 6 is similarly cooled through lines 7 and 8. The reactor is a pressure glass tube having a length of 40 cm and an internal diameter of 25 mm. The supported hydrogenation catalyst contains 0.7% of palladium and 3.0% of zinc on a support comprising an 80:20 w/w ixture of calcium carbonate and alumina. The catalyst is in the form of pellets having a diameter of 3 mm. The dumped height of the catalyst is 27 cm, its bulk, volume being 132 ml and its mass 162 g. At a total pressure of 6 bars and a hydrogenation temperature of 30° C, 36 g of $C_4$ cut to be hydrogenated are fed to the reactor per hour. The amount of $C_4$-hydrocarbon mixture recycled is 360 g/hr. The hydrogenating gas used is a mixture of 65.5% by volume of nitrogen and 34.5% by volume of hydrogen. This hydrogenating gas is fed at a rate of 10.6 g/hr. The hydrogen content of the residual gas is 0.6% by volume.

EXAMPLE 2

Example 1 is repeated except that instead of using a hydrogenation gas produced by diluting hydrogen with nitrogen, use is made of undiluted hydrogen at a rate of 0.2 g/hr, the total pressure being 3.95 bars. The hydrogenated $C_4$-hydrocarbon mixture discharged has the following composition (in percentages by volume):

n-butane: 3.8
isobutane: 0.65
butene-1/isobutene: 39.6
cis-butene-2: 6.7
trans-butene-2: 5.4
butadiene-1,2: 3.15
butadiene-1,3: 36.8
vinylacetylene: 2.6
butyne-1: 1.3.

EXAMPLE 3

Example 2 is repeated except that the $C_4$ cut used is one containing 5% by weight of N-methylpyrrolidone, this $C_4$ cut diluted with N-methylpyrrolidone being fed to the reactor at a rate of 36 g/hr. The composition of the $C_4$ cut (calculated as solvent-free) is the same as the composition of the $C_4$ cut used in Example 2. The total pressure is 3.85 bars. The hydrogenated $C_4$-hydrocarbon mixture discharged has the following composition (in percentages by volume):

n-butane: 4.15
isobutane: 0.6
butene-1/isobutene: 38.5
cis-butene-2: 7.3
trans-butene-2: 5.85
butadiene-1,2: 3.35
butadiene-1,3: 35.8
vinylacetylene: 3.0 butyne-1: 1.45.

We claim:

1. A process for the recovery of 1,3-butadiene, using a selective solvent, from a $C_4$-hydrocarbon mixture containing 1,3-butadiene, hydrocarbons which are more soluble in the selective solvent than 1,3-butadiene, including higher acetylenes and hydrocarbons which are less soluble in the selective solvent than 1,3-butadiene, which comprises: separating the $C_4$-hydrocarbon mixture in a first extractive distillation zone into a distillate containing the less soluble hydrocarbons and an extract of 1,3-butadiene, the more soluble hydrocarbons and the selective solvent; removing the selective solvent from the extract to obtain a mixture of 1,3-butadiene and the more soluble hydrocarbons; passing the mixture of 1,3-butadiene and the more soluble hydrocarbons through a second extractive distillation zone to obtain 1,3-butadiene as a distillate and an extract containing the more soluble hydrocarbons including the higher acetylenes and a residue of 1,3-butadiene and the selective solvent; recovering from the extract a stream containing the more soluble hydrocarbons including the higher acetylenes and 1,3-butadiene having a content of acetylenes of from 10 to 60% by weight; subjecting the acetylenes-containing stream to selective catalytic hydrogenation in the presence of hydrogen and a hydrogenation catalyst to selectively hydrogenate the acetylenes; and adding the hydrocarbon stream obtained after hydrogenation to the starting $C_4$-hydrocarbon mixture.

2. A process as set forth in claim 1 wherein any 1,2-butadiene and $C_5$-hydrocarbons present in the hydrocarbon stream obtained after hydrogenation are removed therefrom prior to addition of said stream to the starting $C_4$-hydrocarbon mixture by distillation.

3. A process as set forth in claim 1, wherein the hydrogenation is carried out in the liquid phase.

4. A process as set forth in claim 1, wherein a bleed stream of the hydrogenated hydrocarbon stream is cooled and recycled to the inlet of the hydrogenation zone, where it is mixed with unhydrogenated hydrocarbon mixture which may or may not be diluted with a mixture of saturated and/or monoolefinically unsaturated hydrocarbons.

5. A process as set forth in claim 1, wherein a hydrogenation catalyst is used which contains a metal in group VIII of the Periodic Table and at least one compound of a metal in group II(b) of the Periodic Table on a support.

6. A process as set forth in claim 1, wherein the hydrocarbon stream to be hydrogenated still contains selective solvent.

7. A process as set forth in claim 1, wherein the hydrogenation is carried out at temperatures of from 5° to 60° C.

8. A process as set forth in claim 1 wherein said selective solvent is selected from the group consisting of dimethylformamide, diethylformamide, dimethylacetamide, formylmorpholine, acetonitrile, furfural, N-methylpyrrolidone, butyrolactone, acetone and mixtures thereof with water.

9. A process as set forth in claim 8 wherein the hydrogenation catalyst contains a metal of group VIII of the periodic table.

* * * * *